United States Patent
Godara et al.

(10) Patent No.: US 9,788,889 B2
(45) Date of Patent: Oct. 17, 2017

(54) ELECTROSURGICAL DEVICES AND METHODS

(71) Applicant: Kyphon SÀRL, Neuchâtel (CH)

(72) Inventors: Neil Godara, Milton (CA); Jason Woo, Mississauga (CA); Emily Won, Toronto (CA)

(73) Assignee: Kyphon SÀRL, Neuchâtel (CH)

( * ) Notice: Subject to any disclaimer, the term of this patent is extended or adjusted under 35 U.S.C. 154(b) by 0 days.

(21) Appl. No.: 14/928,568

(22) Filed: Oct. 30, 2015

(65) Prior Publication Data

US 2016/0045256 A1    Feb. 18, 2016

Related U.S. Application Data

(62) Division of application No. 13/643,310, filed as application No. PCT/CA2011/050203 on Apr. 15, 2011, now Pat. No. 9,173,700.

(Continued)

(51) Int. Cl.
  *A61B 18/14* (2006.01)
  *A61B 18/00* (2006.01)
  *A61B 18/12* (2006.01)

(52) U.S. Cl.
  CPC ............ *A61B 18/148* (2013.01); *A61B 18/14* (2013.01); *A61B 18/1402* (2013.01);
  (Continued)

(58) Field of Classification Search
  CPC ... A61B 18/14; A61B 18/1402; A61B 18/148; A61B 18/1482; A61B 18/1485;
  (Continued)

(56) References Cited

U.S. PATENT DOCUMENTS 3,224,436 A * 12/1965 Le Massena ...... A61B 5/14539
                                                    204/420
3,447,161 A *  6/1969 Weikel .............. A61M 39/0247
                                                    174/47

(Continued)

FOREIGN PATENT DOCUMENTS

WO    2007113866    10/2007

OTHER PUBLICATIONS

International Report on Patentability for Application: PCT/CA2011/050203 dated Oct. 30, 2012.

(Continued)

*Primary Examiner* — Christopher A Flory

(57) ABSTRACT

An electrosurgical probe with internal cooling for use in systems and methods for lesioning in bone and other tissue is disclosed. The probe includes a distal electrical insulator, a proximal electrical insulator, a distal electrical conductor defining a distal electrode with a closed distal end and a proximal electrical conductor defining a proximal electrode, the distal electrode longitudinally spaced apart and electrically isolated from the proximal electrode by the distal electrical insulator. The distal electrode has a closed proximal end formed by a distal face of the distal electrical insulator to thereby define a closed distal inner lumen for circulating the cooling fluid. The proximal electrode has a closed distal end formed by a proximal face of the distal electrical insulator and a closed proximal end formed by a distal face of the proximal electrical insulator to thereby define a closed proximal inner lumen for circulating the cooling fluid.

20 Claims, 6 Drawing Sheets

Related U.S. Application Data

(60) Provisional application No. 61/328,118, filed on Apr. 26, 2010.

(52) U.S. Cl.
CPC ...... *A61B 18/1482* (2013.01); *A61B 18/1485* (2013.01); *A61B 2018/00005* (2013.01); *A61B 2018/00023* (2013.01); *A61B 2018/0044* (2013.01); *A61B 2018/00565* (2013.01); *A61B 2018/00577* (2013.01); *A61B 2018/00791* (2013.01); *A61B 2018/00797* (2013.01); *A61B 2018/126* (2013.01)

(58) Field of Classification Search
CPC  A61B 2018/00005; A61B 2018/00023; A61B 2018/0044; A61B 2018/00791; A61B 2018/00797
USPC .............................................. 606/25, 34, 41
See application file for complete search history.

(56) References Cited

U.S. PATENT DOCUMENTS

| | | | |
|---|---|---|---|
| 4,674,499 A | 6/1987 | Pao | |
| 4,849,596 A * | 7/1989 | Riordan | B23K 11/163 219/56.1 |
| 5,300,068 A * | 4/1994 | Rosar | A61B 18/1492 606/32 |
| 5,300,069 A * | 4/1994 | Hunsberger | A61B 18/1482 606/29 |
| 5,766,167 A * | 6/1998 | Eggers | A61B 18/1445 606/42 |
| 5,807,395 A * | 9/1998 | Mulier | A61B 18/1492 604/22 |
| 6,129,726 A | 10/2000 | Edwards et al. | |
| 6,398,782 B1 * | 6/2002 | Pecor | A61B 18/1492 604/104 |
| 6,524,308 B1 | 2/2003 | Muller et al. | |
| 6,558,379 B1 * | 5/2003 | Batchelor | A61B 18/1482 604/21 |
| 7,216,001 B2 | 5/2007 | Hacker et al. | |
| 7,435,250 B2 * | 10/2008 | Francischelli | A61B 18/1445 606/49 |
| 8,167,878 B2 * | 5/2012 | VanDusseldorp, Sr. | A61B 18/149 606/48 |
| 9,173,700 B2 * | 11/2015 | Godara | A61B 18/148 |
| 9,241,760 B2 * | 1/2016 | Godara | |
| 2001/0025177 A1 * | 9/2001 | Woloszko | A61B 18/12 606/41 |
| 2002/0077627 A1 | 6/2002 | Johnson et al. | |
| 2003/0045870 A1 * | 3/2003 | Madsen | A61B 18/1492 606/40 |
| 2003/0083655 A1 * | 5/2003 | Van Wyk | A61B 18/1402 606/41 |
| 2003/0093007 A1 | 5/2003 | Wood | |
| 2003/0130711 A1 | 7/2003 | Pearson et al. | |
| 2003/0149407 A1 * | 8/2003 | DiResta | A61N 1/325 604/313 |
| 2003/0212394 A1 | 11/2003 | Pearson et al. | |
| 2004/0030333 A1 * | 2/2004 | Goble | A61B 17/3423 606/41 |
| 2004/0167517 A1 | 8/2004 | Desinger et al. | |
| 2005/0070894 A1 * | 3/2005 | McClurken | A61B 18/1492 606/48 |
| 2005/0177209 A1 | 8/2005 | Leung et al. | |
| 2005/0177210 A1 * | 8/2005 | Leung | A61B 18/148 607/101 |
| 2005/0192564 A1 | 9/2005 | Cosman et al. | |
| 2006/0064101 A1 * | 3/2006 | Arramon | A61B 17/32002 606/82 |
| 2006/0111706 A1 | 5/2006 | Truckai et al. | |
| 2006/0178666 A1 * | 8/2006 | Cosman | A61B 18/148 606/41 |
| 2006/0217705 A1 * | 9/2006 | Godara | A61B 18/148 606/41 |
| 2007/0016185 A1 | 1/2007 | Tullis et al. | |
| 2007/0027449 A1 | 2/2007 | Godara et al. | |
| 2007/0123824 A1 * | 5/2007 | Kaveckis | A61B 17/0057 604/118 |
| 2007/0203551 A1 * | 8/2007 | Cronin | A61B 18/18 607/101 |
| 2007/0265617 A1 * | 11/2007 | Falkenstein | A61B 18/1492 606/48 |
| 2008/0015561 A1 * | 1/2008 | Abboud | A61B 18/02 606/20 |
| 2008/0033418 A1 | 2/2008 | Nields et al. | |
| 2008/0065062 A1 * | 3/2008 | Leung | A61B 18/1206 606/41 |
| 2008/0077128 A1 * | 3/2008 | Woloszko | A61B 5/01 606/41 |
| 2008/0097429 A1 * | 4/2008 | McClurken | A61B 18/1492 606/50 |
| 2008/0103504 A1 | 5/2008 | Schmitz et al. | |
| 2008/0172117 A1 * | 7/2008 | Skubitz | A61N 1/0558 607/117 |
| 2008/0249350 A1 * | 10/2008 | Marchitto | A61B 18/14 600/10 |
| 2008/0294155 A1 * | 11/2008 | Cronin | A61B 18/18 606/33 |
| 2009/0005775 A1 * | 1/2009 | Jones | A61B 18/1492 606/41 |
| 2009/0024124 A1 * | 1/2009 | Lefler | A61B 18/1482 606/41 |
| 2009/0054962 A1 * | 2/2009 | Lefler | A61B 18/1482 607/117 |
| 2009/0156981 A1 | 6/2009 | Fay et al. | |
| 2009/0204060 A1 * | 8/2009 | Desinger | A61B 18/1492 604/21 |
| 2009/0326527 A1 * | 12/2009 | Ocel | A61B 5/042 606/33 |
| 2010/0049190 A1 | 2/2010 | Long et al. | |
| 2010/0125269 A1 * | 5/2010 | Emmons | A61B 18/1815 606/33 |
| 2010/0152725 A1 | 6/2010 | Pearson et al. | |
| 2010/0204687 A1 * | 8/2010 | Abboud | A61B 18/02 606/21 |
| 2010/0331883 A1 * | 12/2010 | Schmitz | A61B 10/0275 606/249 |
| 2011/0077451 A1 * | 3/2011 | Marchitto | A61B 18/14 600/13 |
| 2011/0077646 A1 * | 3/2011 | Dahla | A61B 18/1402 606/50 |
| 2011/0152855 A1 * | 6/2011 | Mayse | A61B 18/1492 606/33 |
| 2011/0319880 A1 * | 12/2011 | Prakash | A61B 18/1815 606/33 |
| 2012/0172858 A1 * | 7/2012 | Harrison | A61B 18/1477 606/33 |
| 2013/0012940 A1 * | 1/2013 | Desinger | A61B 18/1492 606/50 |
| 2013/0041369 A1 * | 2/2013 | Godara | A61B 18/148 606/34 |
| 2013/0060244 A1 | 3/2013 | Godara et al. | |
| 2013/0085488 A1 * | 4/2013 | Brannan | A61B 18/18 606/33 |
| 2013/0296647 A1 * | 11/2013 | Mayse | A61B 18/1492 600/104 |
| 2013/0331835 A1 * | 12/2013 | Leung | A61B 18/1206 606/33 |
| 2014/0081260 A1 * | 3/2014 | Cosman, Jr. | A61B 18/1477 606/41 |
| 2014/0128861 A1 * | 5/2014 | Leung | A61B 18/148 606/33 |
| 2014/0303619 A1 * | 10/2014 | Pappone | A61M 25/003 606/41 |
| 2016/0113704 A1 * | 4/2016 | Godara | A61B 18/148 606/41 |

(56) References Cited

U.S. PATENT DOCUMENTS

OTHER PUBLICATIONS

Restriction Requirement and Response for U.S. Appl. No. 13/660,353.
Non-Final Office Action and Response for U.S. Appl. No. 13/660,353.
Non-Final Office Action for U.S. Appl. No. 13/660,353.
Restriction Requirement and Response for U.S. Appl. No. 13/643,310, dated Sep. 25, 2014.
Non-Final Office Action for U.S. Appl. No. 13/643,310, dated Dec. 15, 2014.

* cited by examiner

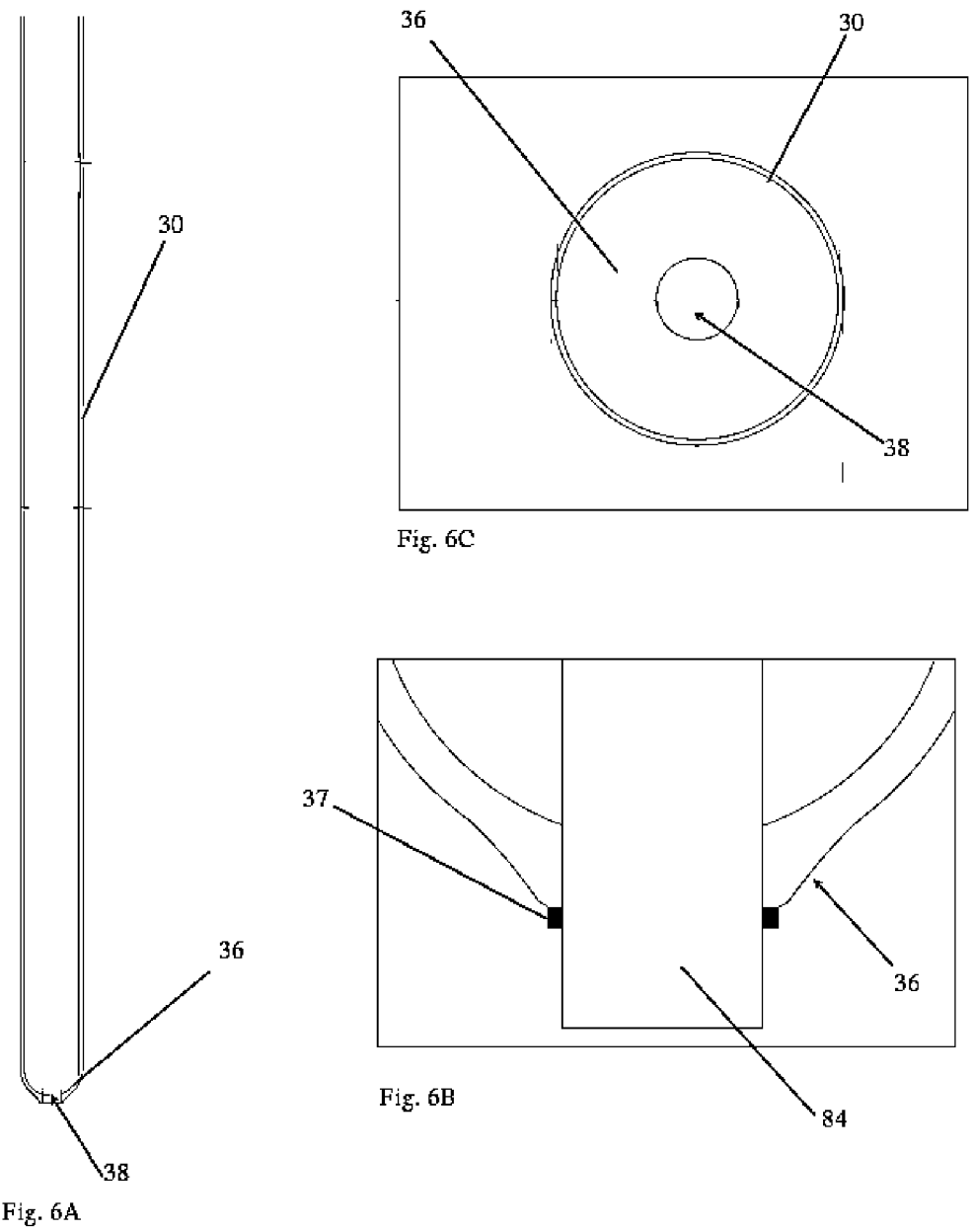

ELECTROSURGICAL DEVICES AND METHODS

TECHNICAL FIELD

The disclosure relates to an electrosurgical device. More specifically, the disclosure relates to an electrosurgical probe and methods of use thereof.

BACKGROUND

US application 20070016185 to Tullis et al is for an electrosurgical system. It discloses an electrode assembly for lesioning that includes an electrode surrounded by layers of insulation and tubing but does not disclose cooling of the lesioning electrode.

Desinger et al (US 2004/0167517) discloses a probe having two distal region electrodes with the distal electrode tip having a cone shape that extends distally. Fluid in the lumen of the probe is spaced apart from the furthest point of the distal tip electrode.

Fay et al (US 2009/0156981) discloses a flexible catheter having a plastic tip and a plastic shaft tube with electrodes attached to it.

Some prior art bi-polar probes, such as those described in US application 2004/0167517 to Desinger et al and in US application 2009/0156981 to Fay et al, have configurations that allow cooling fluid to contact both the active electrode and the return electrode. As cooling fluid often has some conductivity, the flow of coolant between the electrodes will cause some energy to be transmitted within the probe rather than to surrounding tissue, resulting in a loss of effectiveness and possible safety concerns. The stray energy can also affect impedance measurements, causing further problems for devices that measure impedance.

SUMMARY

A bipolar probe used for lesioning in tissue can be cooled by including tubular electrodes configured such that the inner surface of each electrode is cooled while keeping the electrodes electrically isolated. By providing such a probe the coolant is contained in a volume that is electrically isolated from at least one of the electrodes whereby the fluid does not form a conductive link between the electrodes. The probe can include a means for temperature monitoring, which may be particularly useful when used in tissue that hinders the predictability of lesioning, such as electrically insulative tissue.

Thus, for example, embodiments of the present invention include an electrosurgical probe comprising at least two electrically isolated conductors and a lumen for circulating a cooling fluid within only one of said at least two electrically isolated conductors, such that only one of the conductors is directly cooled by the cooling fluid. The cooling fluid circulating within the one conductor nonetheless functions to reduce the temperature of the at least two electrically isolated conductors.

In a first broad aspect, embodiments of the present invention are for an electrosurgical probe comprising the following: at least two electrically isolated electrical conductors, including an inner electrical conductor and an outer electrical conductor. The inner electrical conductor defines a lumen for the circulation of a cooling fluid therein. An inner electrical insulator disposed between the electrical conductors electrically isolates the electrical conductors with the electrical insulator having sufficient thermal conductivity to allow for cooling of the at least two electrical conductors when the cooling fluid is circulating within the lumen of the inner electrical conductor. It is optional that the inner electrical insulator has a thickness of about 0.0254 mm (0.001").

Some embodiments of the first broad aspect include an outer electrical insulator disposed on the outer electrical conductor, the outer and inner electrical conductors being elongated, the inner electrical conductor being disposed coaxially within the outer conductor, and the inner conductor having a closed distal end.

The first broad aspect also includes embodiments wherein a distal portion of the inner conductor is exposed to define a distal electrode, and a distal portion of the outer conductor is exposed to define a proximal electrode.

Some embodiments further comprise a first temperature sensor that is proximate the distal electrode or is positioned at or adjacent to the distal electrode. The first temperature sensor can protrude from a surface of the distal electrode for enhancing isolation from the cooling fluid circulating within the inner conductor lumen. Embodiments can include a second temperature sensor, and, in some specific embodiments, the first temperature sensor is proximate the distal electrode and the second temperature sensor is proximate the proximal electrode.

In some embodiments of the first broad aspect, when in use, the cooling fluid circulates within the inner electrical conductor lumen to contact a portion of an inner surface of the inner electrical conductor for direct cooling of the inner electrical conductor. The inner electrical insulator contacts the outer electrical conductor and the inner electrical conductor, whereby the cooling fluid circulating within the inner electrical conductor lumen indirectly cools the outer electrical conductor. In some such embodiments, a thickness of the outer electrical conductor is substantially constant along its length and a thickness of the inner electrical conductor is substantially constant along its length.

The first broad aspect also includes some embodiments wherein a surface area of the portion of the inner electrical conductor configured to directly contact the cooling fluid is larger than a surface area of an outer surface of the distal electrode and an inner surface of the outer electrical conductor that is indirectly cooled by the cooling fluid has an area larger than an outer surface of the proximal electrode.

Some embodiments further comprise a fluid inlet tube coupled to the inner electrical conductor lumen for supplying the cooling fluid, a fluid outlet tube coupled to the inner electrical conductor lumen to allow the cooling fluid to exit with the option that the fluid outlet tube extend along a majority of the length of the inner electrical conductor lumen. Some embodiments have a distal end of the fluid inlet tube which is proximate the proximal electrode. The fluid outlet tube can extend along a majority of the length of the inner electrical conductor lumen.

In some embodiments of the first broad aspect, the inner electrical insulator is exposed beyond the distal edge of the proximal electrode to define an exposed inner electrical insulator. In some particular embodiments, the distal electrode, the exposed inner electrical insulator, and the proximal electrode have a length ratio of about 1:1:1 wherein it is possible that distal electrode has a length of about 10 mm, the exposed inner electrical insulator has a length of about 10 mm, and the proximal electrode has a length of about 10 mm. In other embodiments, the distal electrode, the exposed inner electrical insulator, and the proximal electrode have a length ratio of about 2:1:2, with the possibility that the distal electrode has a length of about 4 mm, the exposed inner electrical insulator has a length of about 2 mm, and the proximal electrode has a length of about 4 mm. In yet other embodiments, the distal electrode, the exposed inner electrical insulator, and the proximal electrode have a length ratio of about 7:6:7, wherein the distal electrode has a length of about 7 mm, the exposed inner electrical insulator has a length of about 6 mm, and the proximal electrode has a length of about 7 mm.

In a second broad aspect, embodiments of the present invention are for an electrosurgical probe comprising the following: a distal electrical conductor defining a distal electrode with a closed distal end and a proximal electrical conductor defining a proximal electrode, with the distal electrode longitudinally spaced apart and electrically isolated from the proximal electrode by a distal electrical insulator. The distal electrode has a closed proximal end formed by a distal face of the distal electrical insulator to thereby define a closed distal inner lumen for circulating a cooling fluid. The proximal electrode has a closed distal end formed by a proximal face of the distal electrical insulator and a closed proximal end formed by a distal face of a proximal electrical insulator to thereby define a closed proximal inner lumen for circulating a cooling fluid.

In some embodiments of the second broad aspect, the probe further comprises a first fluid inlet tube for supplying the distal inner lumen and a first fluid outlet tube for exit of fluid therefrom, and a second fluid inlet tube for supplying the proximal inner lumen and a second fluid outlet tube for exit of fluid therefrom.

The second broad aspect includes some embodiments wherein the distal electrode and the proximal electrode have substantially the same diameter. In some embodiments, the distal and proximal electrical conductors are elongated.

Some embodiments comprise a first temperature sensor located, in some specific embodiments, proximate the distal electrode or, in alternate embodiments, positioned at or adjacent to the distal electrode. The first temperature sensor can protrude from a surface of the distal electrode for enhancing isolation from the cooling fluid circulating within the distal inner lumen.

Probes of the second aspect can further comprise a second temperature sensor, and, in some specific embodiments, the first temperature sensor is proximate the distal electrode and the second temperature sensor is proximate the proximal electrode.

In some embodiments of the second broad aspect, when the probe is in use, the cooling fluid circulating within the distal inner lumen contacts a portion of an inner surface of the distal electrical conductor for direct cooling of the distal electrical conductor and the cooling fluid circulating within the proximal inner lumen contacts a portion of an inner surface of the proximal electrical conductor for direct cooling of the proximal electrical conductor.

In some embodiments, a thickness of the proximal electrical conductor is substantially constant along its length, and, alternatively or in addition, a thickness of the distal electrical conductor is also substantially constant along its length.

In some embodiments of the second broad aspect the distal and the proximal electrical conductors are electrically conductive along their lengths. Furthermore a surface area of the distal electrical conductor configured to directly contact the cooling fluid can be substantially similar to an area of an outer surface of the distal electrode. Also, a surface area of the proximal electrical conductor configured to directly contact the cooling fluid can be substantially similar to an area of an outer surface of the proximal electrode.

In a third broad aspect, embodiments of the present invention include a system comprising the following: an electrosurgical generator, a source of cooling fluid, and at least one electrosurgical probe. An electrosurgical probe comprises the following: at least two electrically isolated electrical conductors, including an inner electrical conductor and an outer electrical conductor, the inner one of the electrical conductors defining a lumen for the circulation of a cooling fluid therein, and an inner electrical insulator disposed between the inner and outer electrical conductors for electrically isolating the electrical conductors. The inner electrical insulator has sufficient thermal conductivity to allow for cooling of the at least two electrical conductors when the cooling fluid is circulating within the lumen of the inner electrical conductor. The probe is operable to be connected to the generator for delivering energy between the inner electrical conductor and the outer electrical conductor in a bipolar manner and the lumen is operable to be connected to the source of cooling fluid for delivering fluid for cooling the inner and outer electrical conductors.

Some embodiments of the third aspect include a distal portion of the inner electrical conductor of the probe exposed to define a distal electrode. In some embodiments, the electrosurgical probe further comprises a first temperature sensor with the first temperature sensor being located proximate the distal electrode.

Some embodiments comprise a distal portion of the outer electrical conductor being exposed to define a proximal electrode. The at least one electrosurgical probe further comprises a second temperature sensor, with the second temperature sensor being proximate the proximal electrode.

In some embodiments, the electrosurgical generator is operable to deliver radiofrequency energy.

In some embodiments of the third aspect, the electrosurgical generator comprises a controller for monitoring the first temperature sensor and adjusting the energy delivered based on the sensed temperature.

In a fourth broad aspect, embodiments of the present invention include a method of lesioning in bone tissue, the method comprising the following steps: providing a bipolar probe having an active tip comprising at least two electrodes for delivering energy, advancing the active tip into a bone tissue, delivering energy between the at least two electrodes in a bipolar manner whereby energy is delivered to tissue, and supplying cooling fluid to the active tip for internal cooling of the at least two electrodes.

Some embodiments further comprise selecting a temperature for the cooling fluid that is supplied to the active tip wherein the temperature selected for the cooling fluid can be from just above 0 degrees C. to about 30 degrees C. Such methods can further comprise adjusting the flow rate of the cooling fluid.

Some embodiments of the fourth broad aspect include monitoring the temperature of tissue that the energy is delivered to and, in certain embodiments, controlling the delivery of energy using the temperature of the tissue that the energy is delivered to.

In further embodiments of the fourth aspect, the bone is a vertebral body, the energy is delivered to a nervous tissue generating pain signals at the bone-tumor interface, and/or the active tip is advanced the into a trabecular bone.

Some methods according to the fourth aspect of the invention include an assembly comprising a cannula with a stylet disposed within. The assembly is used to advance the probe into the vertebral body, and the stylet is withdrawn from the cannula subsequent to the introducer assembly being advanced into the vertebral body.

In some embodiments of the fourth broad aspect, the polarity of the energy delivered to the at least two electrodes is reversible.

Some embodiments of the fourth aspect relating to the polarity of the probes being reversible include methods comprising emitting a stimulation pulse comprising a continuous train of biphasic waves at a set frequency, navigating the active tip through tissue, reversing the polarity of the at least two electrodes to identify which electrode a stimulated nerve is in proximity to, and repeating the previous steps until the location of the nerve is determined.

Some other embodiments of the fourth aspect relating to the polarity of the probes being reversible include methods comprising the following: delivering energy to at least two electrodes for ablation, and reversing the polarity of the energy to the at least two electrodes. The method can include each probe being active for about 50 percent of the time.

Some embodiments of the fourth aspect relating to monitoring tissue temperature include methods comprising placing at least one external temperature sensor at the boundary of a desired lesion, monitoring the at least one external temperature sensor during energy delivery, and determining the lesion is complete when the external temperature (the temperature from the sensor at the boundary) reaches a predefined value.

Some embodiments of the fourth broad aspect include methods wherein the energy is delivered to a nerve within a vertebral body, wherein it is optional that the energy is delivered to a basivertebral nerve.

BRIEF DESCRIPTION OF THE DRAWINGS

In order that the invention may be readily understood, embodiments of the invention are illustrated by way of examples in the accompanying drawings, in which:

FIGS. 6a, 6b and 6c are illustrations of a portion of a probe 100, in accordance with an embodiment of the present invention.

DETAILED DESCRIPTION

Figure 1:
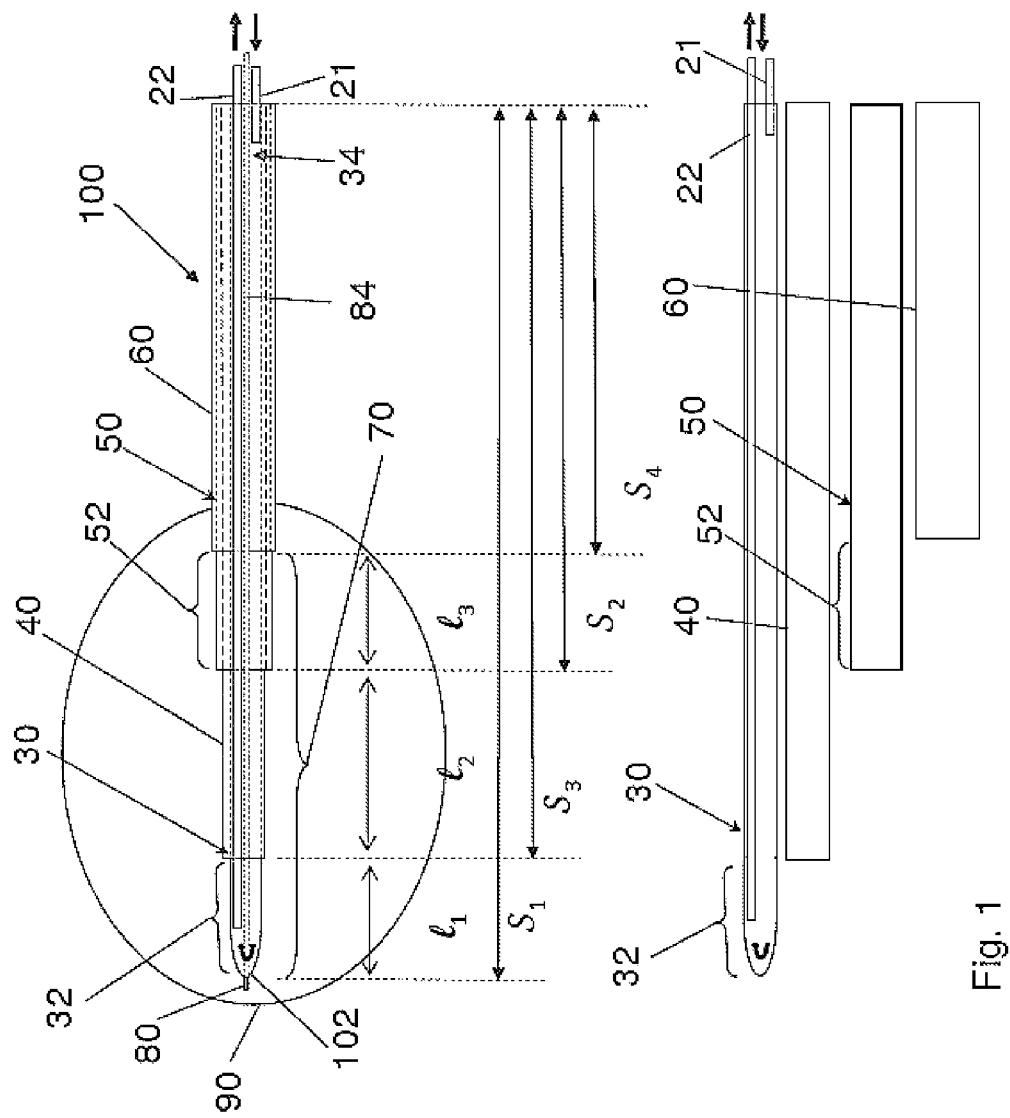
FIG. 1 is an illustration of a probe 100 in accordance with an embodiment of the present invention.

Creating predictable lesions in insulative tissue such as bone can be aided by using a bi-polar probe with internal cooling. Embodiments of such a probe include tubular electrodes configured such that the inner surface of each electrode is cooled, directly or indirectly, while keeping the electrodes electrically isolated. One possible configuration is an electrosurgical probe comprising two electrically isolated electrical conductors with an inner one of the conductors inside of the other and the inner electrical conductor defining a lumen for the circulation of a cooling fluid inside of it. The probe also has an electrical insulator layer between the electrical conductors for electrically isolating the electrical conductors. The electrical insulator has sufficient thermal conductivity to allow for cooling of the outside electrical conductor by cooling fluid circulating within the lumen of the inner electrical conductor. Thus, only one conductor is cooled directly, i.e., in contact with the cooling fluid, while the other conductor is indirectly cooled.

With specific reference now to the drawings in detail, it is stressed that the particulars shown are by way of example and for purposes of illustrative discussion of certain embodiments of the present invention only. Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

FIG. 1 is an illustration of a probe 100 in accordance with an embodiment of the present invention. The probe comprises an inner elongate conductor 30 and an outer elongate conductor 50. The inner and outer conductors 30, 50 each have a hollow tubular configuration and define a lumen there-through. The inner and outer conductors 30, 50 are coupled to an energy supply at proximal ends thereof. In one example, the energy supply may comprise a radiofrequency (RF) energy delivery source and an energy sink. In one specific example, the inner conductor 30 functions as an active electrode and is coupled to an RF energy delivery source, and the outer conductor 50 is coupled to an energy sink such as a ground connection, forming a return electrode. In other words, the inner conductor 30 functions as a control electrode and the outer conductor 50 functions as a neutral or ground reference electrode. In another example, the outer conductor 50 functions as an active electrode and the inner conductor 30 functions as a return electrode. In such embodiments, probe 100 can be operated in a bipolar manner, where energy is delivered substantially between conductors 30, 50. The inner and outer conductors 30, 50 may be connected to the RF energy delivery source and ground via an electrical connection through a probe handle 8, shown in FIG. 2a, which may be coupled to a proximal end of probe 100. The inner conductor 30 is disposed coaxially within the lumen of the outer conductor 50. The inner and the outer conductors 30, 50 each comprise an electrically conductive portion at least along a length thereof and more specifically, at least along a distal segment of conductors 30, 50. Each of the electrically conductive portions is coupled to an energy supply through an electrically conductive pathway.

In FIG. 1, the inner conductor 30 and the outer conductor 50 are electrically conductive along their length. In one example as shown in FIG. 1, the inner conductor 30 has a length S1, and the outer conductor 50 has a length S2. In one example, the inner and the outer conductors 30, 50 each comprise a stainless steel hypotube. In another example, the inner and outer conductors 30, 50 may comprise an electrically conductive, biocompatible material such as titanium or nitinol. The inner conductor 30 is electrically isolated from the outer conductor 50 by an inner insulator 40 disposed between the inner conductor 30 and the outer conductor 50. In some embodiments, the inner insulator 40 extends longitudinally along at least the entire length of the outer conductor 50. In some embodiments, it has a length that is greater than the length of the outer conductor 50. In one example, as shown in FIG. 1, the inner insulator has a length S3 that is greater than length S2 of the outer conductor 50. In some embodiments, the inner insulator 40 is electrically insulative and thermally conductive. In the illustrated embodiments, the distal most portion of the inner conductor 30 is exposed at the distal tip thereof and forms a distal electrode 32 having a length L1.

The inner elongate conductor 30 as shown in FIG. 1 and FIG. 2b has a closed distal end and defines a lumen 34 there-through for circulating a cooling fluid. The term "circulate" relates to fluid that mostly moves or is caused to move through a generally closed system in a controlled manner rather than fluid that enters and mostly passes through the system to the outside environment, such as passing through an open ended tube. A fluid inlet tube 21 may be disposed within the lumen 34 to supply cooling fluid within the inner lumen 34 from a cooling supply (not shown). A fluid outlet tube 22 may be disposed alongside the fluid inlet tube 21 within the inner lumen 34 to allow the cooling fluid to exit via a proximal end of the probe 100. The fluid outlet tube 22 may extend along a majority of the length of the inner conductor 30. In some embodiments, fluid outlet tube 22 may be shorter than fluid inlet tube 21. The outer conductor 50 has an electrical insulator 60 disposed on an outer surface thereof, along at least a portion of the outer conductor 50, whereas a distal portion of the outer conductor 50 remains electrically exposed, forming a proximal electrode 52 with a length L3. In one example, the outer insulator 60 has a length S4 as shown in FIG. 1. In one embodiment the outer insulator 60 may have a length that is substantially the same as the length of the outer conductor 50. The inner insulator 40 is exposed between the distal edge of the proximal electrode 52 and the proximal tip of the distal electrode 32. The length of the exposed insulator is labelled as L2. The region of the probe extending from the proximal electrode 52 to the distal electrode 32 forms an active tip 70. A radiopaque band 72 may be positioned at a proximal end of the active tip 70 as shown in FIG. 2a. The radiopaque band 72 may act as a navigational reference to guide and facilitate positioning the active tip 70 at a target location within a patient's body. In other embodiments, the radiopaque band may be positioned at any location along the active tip 70 or at any location along the probe 100. In still another embodiment, more than one radiopaque band 72 or a radiopaque marker may be positioned along the probe. In one example the radiopaque band 72 may function as a navigational reference under fluoroscopic imaging.

In one example, the proximal electrode 52 is a return electrode and the cooling fluid cools the proximal electrode 52 prior to reaching and cooling the distal electrode 32, which is the active electrode. This may provide a more uniform lesion to be produced when RF energy is supplied to the probe 100. The structure of the probe 100, in one example, allows cooling fluid to indirectly cool the proximal electrode 52 and to directly cool the distal electrode 32. The cooling fluid flows through the inner lumen 34 of the inner conductor 30 and cooling is transmitted indirectly to the proximal electrode 52 through thermal conductivity through a wall of the inner conductor 30 and a wall of the inner insulator 40. Cooling fluid is supplied from the fluid inlet tube 21 which exits into the lumen 34 near the location of the proximal electrode 52. The relatively low temperature of the cooling fluid cools proximal electrode 52 indirectly, thus raising the temperature of the fluid. In other words, the cooling fluid allows heat to be removed from the proximal electrode 52. The fluid then flows within the lumen 34 to the distal electrode 32 at the slightly elevated temperature. Thus, cooling fluid at a lower temperature is used to indirectly cool the proximal electrode 52, whereas, cooling fluid that is at a slightly higher temperature passes through the distal electrode 32 to cool it directly. It is possible that by cooling proximal electrode 52 indirectly at a lower temperature and cooling the distal electrode 32 directly at a slightly higher temperature, cooling of electrodes 32, 52 will be substantially equivalent. This arrangement may allow cooling to be transmitted uniformly to both the proximal and distal electrodes 32, 52, thus allowing a relatively uniform heat distribution around the two electrodes, which may allow a more uniform lesion to be produced when the electrodes 32, 52 are placed in target tissue. Providing cooler fluid to cool the proximal electrode 52 may offset the difference in cooling at the proximal and distal electrodes 32, 52 due to direct and indirect cooling respectively.

In the case of the embodiment of FIG. 1, another factor that can help compensate for distal electrode 32 being directly cooled while proximal electrode 52 is indirectly cooled is that proximal electrode 52 has a larger diameter and circumference. Consequently, for distal and proximal electrodes of equal length, proximal electrode 52 will have a slightly larger inner surface, which will increase the effectiveness of the internal cooling fluid.

In one example, the cooling fluid may comprise water. In another example, the cooling fluid may comprise saline. In an alternate example an alcohol may be used. As a further example, an isopropyl alcohol may be used. In one embodiment, the temperature of the cooling fluid may range from about its freezing point to about room temperature. In one embodiment, the fluid inlet and outlet tubes 21, 22 may be constructed from a metal. In one example the fluid inlet and outlet tubes are made from stainless steel hypotubes and may be connected to the fluid supply at proximal ends thereof with non-conductive supply tubes 12, 14. These may comprise any non-conductive material such as a polymer. In one specific example, the supply tubes 12, 14 comprise polyvinylchloride (PVC) tubing that may be UV (ultraviolet) glued to the stainless steel inlet and outlet tubes 21, 22. In other embodiments, any other means can be used to join the supply tubes to the outlet tubes. In other embodiments the fluid inlet and outlet tubes 21, 22 may be constructed from a non-conductive material such as a polymer. In still other embodiments, the fluid inlet and outlet tubes 21, 22 may be formed of alternate materials. The fluid inlet and outlet tubes 21 and 22 may be positioned alongside each other within the lumen 34 of the inner conductor 30. In other embodiments any flow pathway may be provided to the probe 100 to allow fluid to enter and exit the inner conductor 30. The flow pathway may comprise a fluid inflow path that is separate from a fluid outflow path which provides directional flow. In some embodiments cooling fluid may be directed into the inner conductor 30 directly without use of the fluid inlet tube 21.

In one embodiment the active tip 70 may have a length (L1+L2+L3) that ranges from about 5 mm to about 40 mm. In one example, the length of the distal electrode 32 (L1), the exposed inner insulator 40 (L2), and the proximal electrode 52 (L3) may vary in about a 2:1:2 ratio. In other embodiments the ratio may be in about a 1:1:1 configuration. Alternate embodiments are possible as well. In other embodiments, the lengths L1, L2 and L3 may have a different ratio. In another example, the L1:L2:L3 ratio is about 7:6:7.

Figure 5:
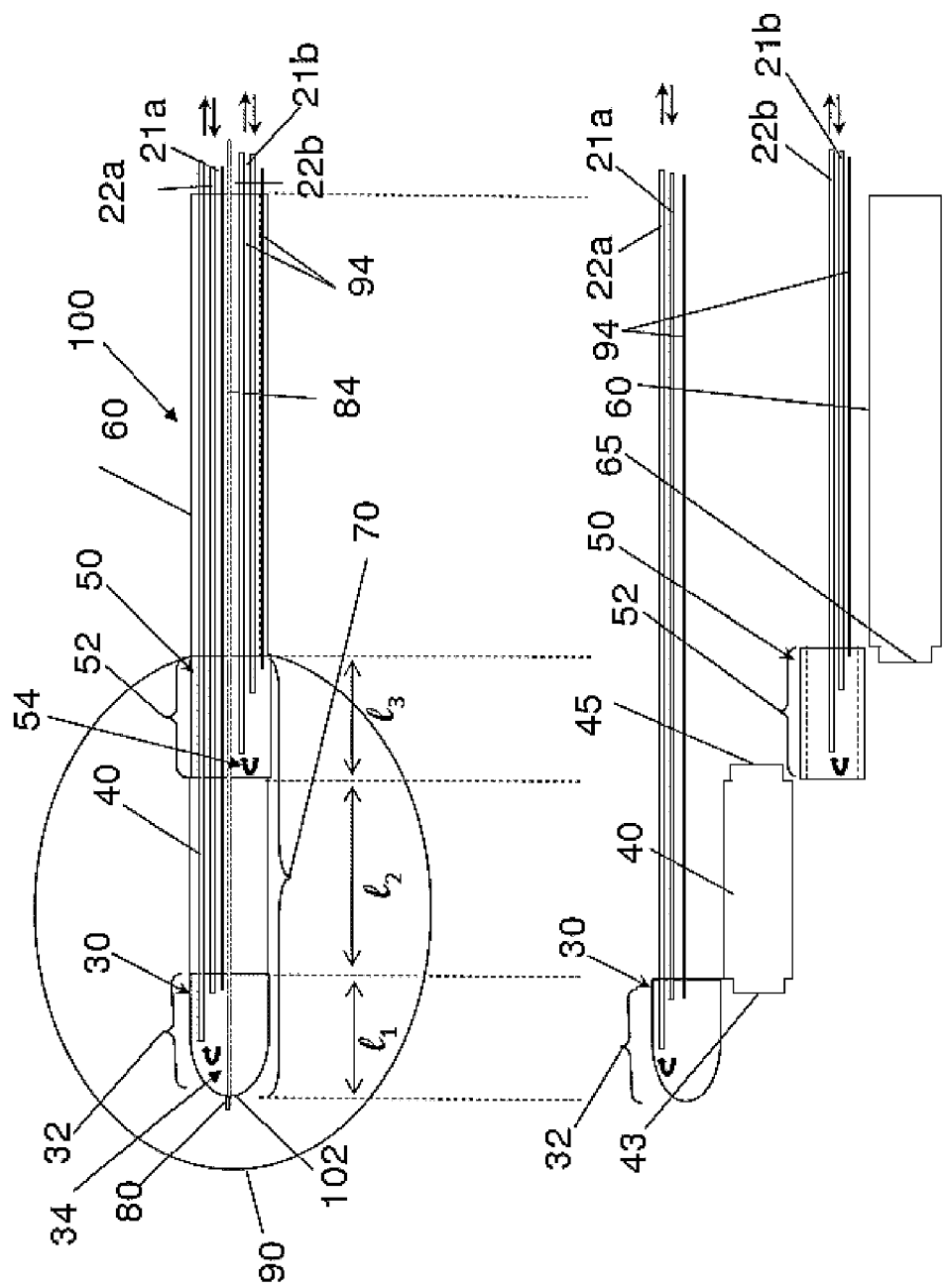
FIG. 5 is an illustration of a probe 100, in accordance with an alternate embodiment of the present invention.

In another embodiment, the inner and outer conductors 30, 50 may only extend along a portion of the probe 100. In one example inner and outer conductors 30, 50 may be electrically conductive along their lengths and may form the proximal and the distal electrodes, 32 and 52. In one specific example, as shown in FIG. 5, only the exposed portions of the inner and outer conductors 30 and 50 are electrically conductive, and the inner and outer conductors 30, 50 may have substantially the same width. The inner and outer conductors may be spaced apart and electrically isolated from each other by an inner insulator 40. In one example the inner insulator 40 may comprise a polymer. In a specific example, the insulator 40 may comprise a substantially rigid plastic insert. In one example the electrically isolated distal and proximal electrodes 32 and 52 may be cooled through separate cooling sources. As shown in FIG. 5, the distal electrode 32 is supplied with a cooling fluid through fluid inlet and outlet tubes 21a and 22a. Whereas, cooling to the proximal electrode 52 is supplied through cooling inlet and outlet tubes 21b and 22b. The fluid inlet and outlet tubes may comprise a non-conductive material such as a polymer. Each of the proximal and distal electrodes 32, 52 are coupled to an energy supply through electrically conductive insulated wires 94.

In this example, the distal and proximal electrodes 32 and 52 each define a closed inner lumen, 34 and 54 respectively, within which cooling fluid flows. The distal electrode 32 has a closed distal end and a closed proximal end formed by co-operative engagement of the distal electrode proximal portion with a distal face 43 of the inner insulator 40, defining the closed inner lumen 34. The proximal electrode 52 has a closed distal end formed by co-operative engagement of the proximal electrode distal end with the proximal face 45 of the inner insulator 40, as shown in FIG. 5. The proximal electrode 52 further has a closed proximal end defined by co-operative engagement of the proximal electrode proximal end with a distal face 65 of the outer insulator 60, defining the closed inner lumen 54. The cooling fluid is restricted within the lumens 34 and 54. The distal face 65 of the outer insulator, as well as the distal 43 and the proximal face 45 of the inner insulator, extend substantially transversally along the width of the probe. The distal face 65 may comprise openings to allow fluid inlet tubes 21a, 21b and fluid outlet tubes 22 a, 22b as well as insulated wires 94 to extend therethrough. Similarly, distal and proximal faces 43 and 45 may provide openings therethrough to allow passage of the inlet and outlet tubes 21a and 21b respectively and one of the insulated wires 94. A seal may be provided around the openings to ensure that cooling fluid is restricted within the lumens 34 and 54.

Figure 2:
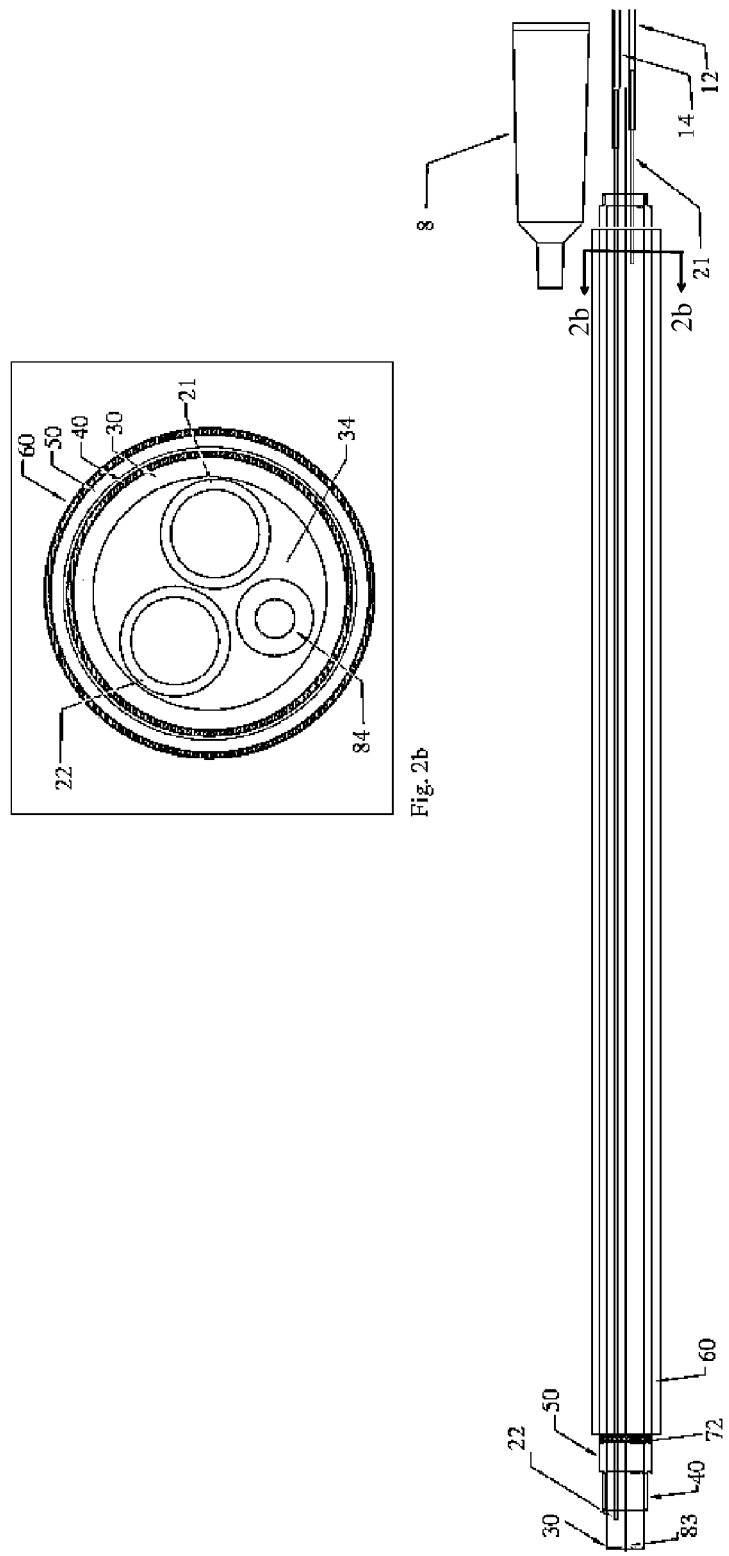
FIG. 2a is a side view of a probe 100, showing various features in transparency for ease of illustration, in accordance with an embodiment of the present invention.
FIG. 2b is a cross-sectional view of probe 100, taken along line 2b-2b of FIG. 2a, in accordance with an embodiment of the present invention.

Additionally, a temperature sensor 80 may be positioned at a location along the probe 100 as shown in FIGS. 1, 2 and 5. In one embodiment the temperature sensor 80 may be positioned substantially adjacent the distal tip 102 of the probe 100. For example, the temperature sensor 80 may protrude from the surface of the distal electrode 32. In other words, temperature sensor 80 may jut out or stick out from a surrounding surface of the probe 100. In other embodiments the temperature sensor 80 may be positioned at any location along the length of the probe. In some embodiments the temperature sensor 80 may be positioned at or adjacent to the active tip 70. In one example, the temperature sensor 80 may comprise a thermocouple. In one specific example, a thermocouple may be formed using a hypotube 84 disposed within the lumen 34 of the inner conductor 30. A constantan wire can be disposed within the thermocouple hypotube 84 to form a thermocouple junction 83 about the distal tip 102, as shown in FIG. 2a. In other embodiments, a thermocouple may be formed using a pair of wires to form a junction. In one example, a thermocouple is positioned at a distal face of the outer electrode 52. In another example, a thermocouple is positioned between the outer electrode 52 and inner insulator 40. In one example, the temperature sensor 80 is coupled to and in communication with a controller for the energy supply, such as an energy supply having an RF energy delivery source. In one example, the temperature sensor 80 may be coupled to a controller at its proximal end via the handle 8.

In some embodiments a second temperature sensor is proximate to proximal electrode 52 and is in communication with a controller for the energy supply for providing additional information. Such an embodiment could be used with a generator capable of monitoring two temperature sensors at one time. Alternatively, a generator capable of monitoring only one temperature at a time could be used if an external device switched between the two (or more) temperature sensors.

Generally, embodiments of the present invention may comprise a plurality of temperature sensors, which may be positioned at different locations on the probe, for example, on or adjacent to the surface of the electrodes, between the electrodes, or at or near the electrodes, proximally or distally. A generator used in a system with two or more temperature sensors would include an algorithm for controlling the output of energy based on multiple temperature readings.

The inner conductor 30 has a closed distal end. As shown in FIGS. 6a, 6b and 6c, in one embodiment, the distal end of the inner conductor 30 is swaged to form a concentrically tapered end 36 with an opening 38 therethrough. The size or diameter of the opening 38 is smaller than a diameter of the inner conductor 30 along its length as shown in FIG. 6c. The opening 38 allows the thermocouple hypotube 84 to extend or protrude from the distal end face of the inner conductor 30. In some embodiments, the thermocouple hypotube 84 may be laser welded to the inner conductor 30 at a wall of the opening 38. In other examples any other means of attachment may be used. In some embodiments where the thermocouple may be positioned at any other location along the probe, the distal end of the inner conductor 30 may be swaged in a similar manner as disclosed above to reduce the size of the opening at the distal end of the inner conductor hypotube 30. The reduced diameter opening may then be closed by laser welding at the distal most end. The closed distal end of the inner conductor 30 may be formed using other means. In some embodiments the closed distal end of the hypotube may comprise a separate end piece or end cap that may be attached to the distal end of the hypotube. In some examples, the end piece may be dome shaped, triangular shaped or may have a flat surface. The end piece may or may not be metal. In other embodiments a closed distal end of the inner conductor may be formed by providing an end piece in the form of a metal insert which may be laser welded to the hypotube distal end. In other embodiments, any other attachment means may be used. In one example, an adhesive may be used to attach the end piece to the hypotube distal end. In one such example, the adhesive may be an ultraviolet (UV) glue.

In some embodiments, the probe size may range from an outer diameter of about 13 Gauge, 2.413 mm (0.095"), to about 17 Gauge, 1.47 mm (0.058"). In one example, the probe 100 has a diameter of about 17 Gauge and has an outer conductor 50 with a length of about 215.9 mm (8.5") and an inner conductor 30 with a length of about 228.6 mm (9.0"). The fluid outlet tube 22 has a length of about 241.3 mm (9.5") and extends into the handle, whereas the fluid inlet tube 21 is about 38.1 mm (1.5") in length and positioned at the proximal end of the inner conductor 30. The thermocouple hypotube 84 is positioned within the inner lumen 34 of inner conductor 30 and has a length of about 254 mm (10").

In one example the insulators 40 and 60 may comprise a polyester. The insulators 40 and 60 may be disposed onto the conductors 30 and 50, respectively, using a heat-shrink procedure. The conductors 30 and 50 may be electrically conductive along their length. In one example, the polyester is a Polyethylene terephthalate (PET). In other embodiments a polyamide, Fluorinated ethylene propylene (FEP) or polytetrafluoroethylene (PTFE), may be used to form one or both of the insulators 40, 60. In one embodiment the insulators 40 or 60 may be provided in the form of a coating or a layer. In still other embodiments PEEK may be used. In one example the thickness of the inner insulator 40 may vary from about 0.0127 mm (0.0005") to about 0.254 mm (0.010"). The thickness of the inner insulator 40 provides sufficient thermal conductivity to allow cooling to be conveyed to the outer conductor 50. This feature allows heat to be removed from the outer conductor 50, which may allow a larger lesion to be produced and minimize charring of tissue. In one specific example, PET is used in insulators 40 and 60, each having a width of about 0.03175 mm (0.00125").

In one embodiment of a method aspect of the present invention, the probe 100 is used to treat a region within a patient's body. In one embodiment, the region may comprise tissue with varying composition. In one such embodiment, the tissue may comprise any one of or a combination of vascular tissue, soft tissue, trabecular bone tissue, cortical bone tissue, fatty tissue, tumor or nervous tissue.

Figure 3:
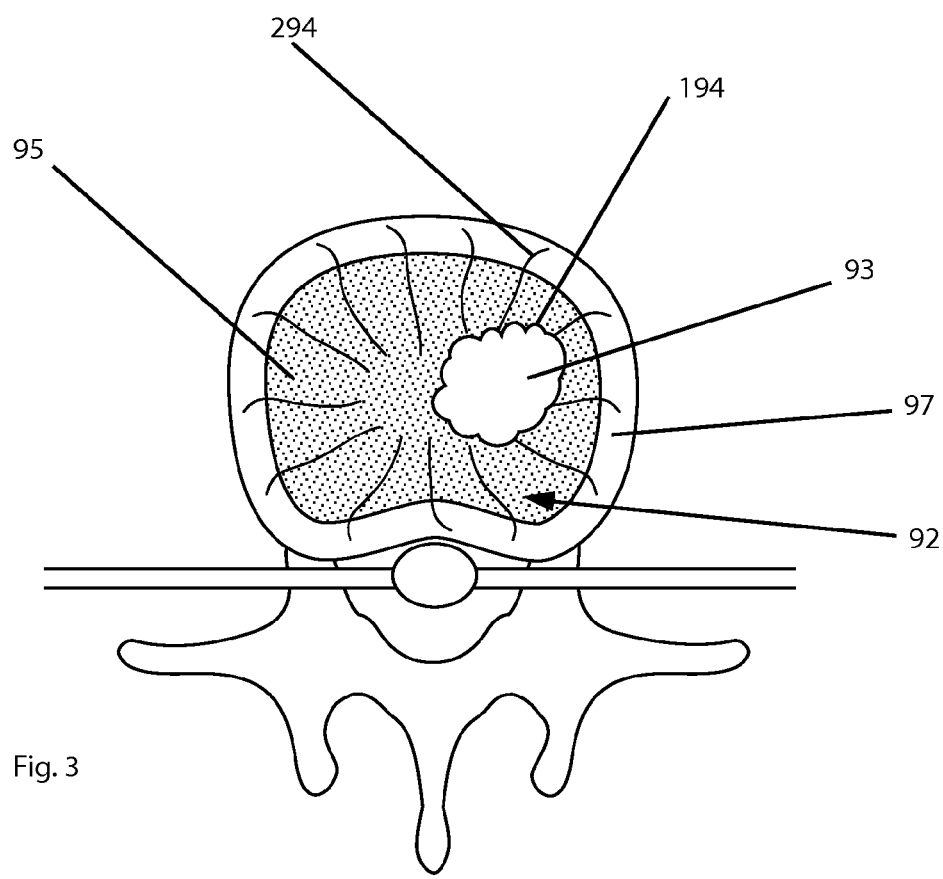
FIG. 3 is an illustration of a target location, in accordance with an embodiment of a method of the present invention.

In one specific embodiment the probe 100 is placed within a vertebral body. For example, as shown in FIG. 3, the probe 100 may be positioned adjacent a tumor 93 within a vertebral body at a bone-tumor interface 194. The probe 100 may be used to destroy nervous tissue generating pain signals at the bone-tumor interface. In one example, the probe 100 is advanced into a vertebral body 92 until the distal end 102 of the probe is positioned at the tumor-nerve interface at the edge of the tumor 93 adjacent nerves 294, as shown in FIG. 3. In one specific example, the probe active tip 70 may be positioned within the trabecular bone 95 within the vertebral body 92 that is encased by the electrically insulative cortical bone 97. In one embodiment, the probe 100 is positioned substantially adjacent the rich nerve supply within the vertebral body. In one embodiment, the probe 100 may be positioned within or substantially adjacent to the vertebral body in proximity to sensitive structures such as the cortical bone that may be non-conductive, or in other words, may have a low electrical conductivity.

Nerve stimulation can be used to position a probe. In bipolar nerve stimulation applications, the stimulation effects are not symmetric about each electrode. One electrode will have a larger stimulation capacity for a given biphasic wave. The electrode that is closest to a stimulated nerve can be identified by reversing the polarity of the bipolar probe, also called manipulating. Balanced stimulation of nerves can be achieved by alternating the polarity in a balanced manner. For example, 10 pulses could be delivered with a first electrode as the control electrode to more intensely stimulate the nerves nearest to it, and then 10 pulses could be delivered with a second electrode as the control electrode. An embodiment of a method using such a procedure to help position a probe includes the following steps: emitting a stimulation pulse comprising a continuous train of biphasic waves at a set frequency, navigating the active tip through tissue, and reversing the polarity of the two electrodes to identify which electrode a stimulated nerve is closest to.

The probe 100 may improve heating capability in the vicinity of a non-conductive structure. The probe 100 provides energy in a bipolar manner and may be used in the vicinity of a cortical bone structure or other non-conductive structures to provide treatment to the non-conductive structure through indirect thermal conduction. Thus, probe 100 may be used to treat structures that are non-conductive in monopolar RF applications, where the energy transmission to a ground may be limited as the non-conductive structure is encountered in the energy pathway to the ground.

In another example, probe 100 may be used to target nerves at other locations within the vertebral body. In still another example, the probe 100 may be positioned substantially adjacent to or in the vicinity of any other bone tissue. In yet another example probe 100 may be used to treat a highly vascular tissue such as liver. In some embodiments, the probe 100 may be used to provide uniform or consistent lesions in the vicinity of bone or variable tissue. In other words, the probe 100 may be used to provide lesions that are substantially homogeneous.

Figure 4A:
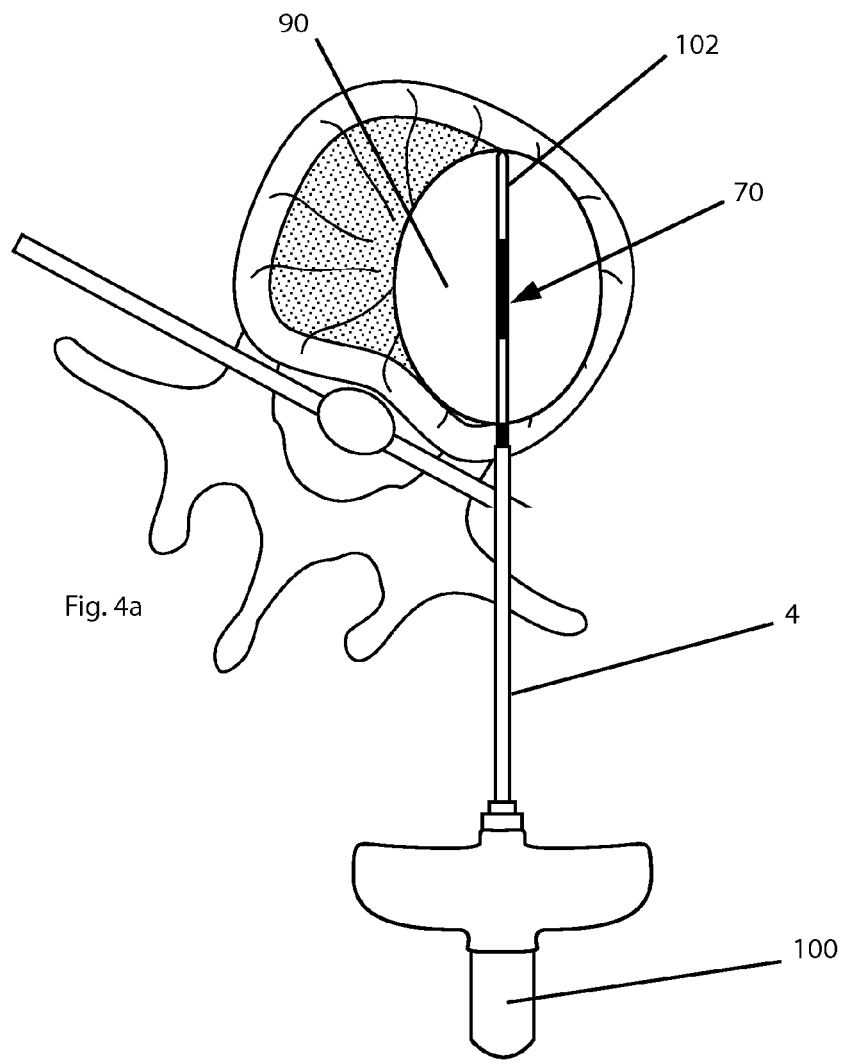
FIGS. 4a and 4b are illustrations of a method in accordance with an embodiment of the present invention.
Figure 4B:
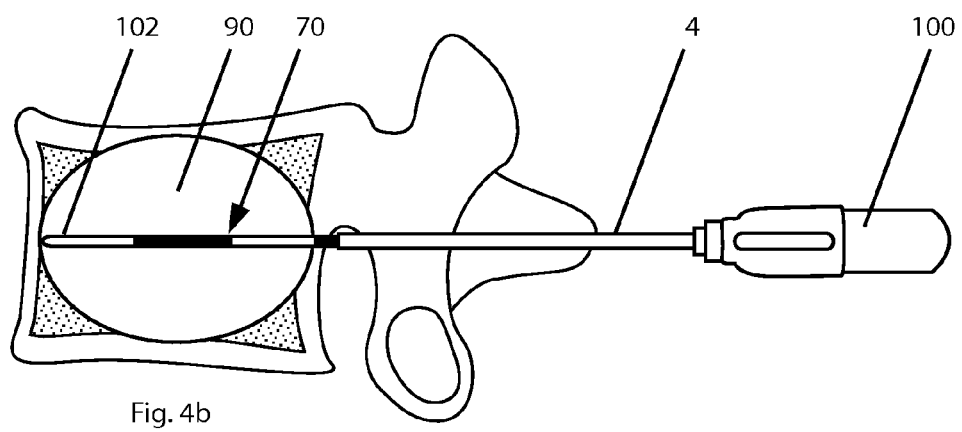

In one particular embodiment, an introducer needle assembly may be inserted and advanced to a target location within a patient's body. The introducer needle assembly may comprise a cannula with a stylet disposed therein. In one example, the target location is a vertebral body as shown in FIGS. 4a and 4b. In such an embodiment, the introducer assembly 4 may be inserted into the vertebral body using a transpedicular approach. The introducer needle assembly may be inserted through the pedicle at an angle of about 15° to about 25° oblique to the mid-saggital plane, which provides a trajectory to access the vertebral body. In another embodiment a lateral approach may be used. In still other embodiments any approach that allows access to the vertebral body may be used. As an example, any conventional approach used in standard vertebroplasty or vertebral augmentation procedures to gain access to the vertebral body may be used. Once the introducer needle assembly has been positioned at the target site, the stylet may be withdrawn from the cannula. The probe 100 may then be inserted through the cannula and advanced to the target site. In some embodiments, the probe 100 can be inserted directly to the target tissue and may include a sharp trocar tip at a distal end of the probe. In one such example, the target tissue is a soft tissue. In another embodiment, a bilateral approach may be used to treat a vertebral body. The probe 100 may be inserted into a vertebral body at a first target location to the right of the mid-saggital plane at an angle of about 15° to about 25° to the mid-saggital plane. A first bi-polar lesion may then be formed at a first location within the vertebral body. The probe 100 may then be inserted at a second target location to the left of the mid-saggital plane at an angle of about 15° to about 25° from the mid-saggital plane. A second bi-polar lesion may then be formed at a second location within the vertebral body. In one such example, the first and second lesions may encompass a majority of the vertebral body.

Bipolar lesions of different geometry can be created by manipulating the duration and intensity of energy delivered through each electrode as the control electrode. This is related to the higher tissue temperatures being found around the control electrode. Manipulating a bipolar probe can create lesions that are peanut, mushroom or symmetric ellipsoid shaped. Keeping each electrode active for 50 percent of the time can help in creating symmetrical or more symmetrical lesions.

In one example, RF energy is supplied by an RF generator in a bipolar manner to probe 100. The power output of the RF generator may be temperature controlled. In one embodiment, direct tissue temperature monitoring is used in conjunction with internal cooling when supplying RF power to form a lesion. The power output may be adjusted based on the measured temperature response of the tissue to RF heating under cooling. The temperature response of the target tissue may be monitored using the temperature sensor 80.

One embodiment is for a system in which the user puts the selected coolant temperature into the system from a range from just above 0° C. up to about 30° C. The cooling fluid is delivered by a pump unit, which is controlled by the same generator that delivers energy. The flow rate (and correspondingly the amount of cooling) can be adjusted based on tissue characteristics and the intended lesion geometry.

The RF energy is delivered in a bipolar manner between conductors 30 and 50 and allows a lesion 90 to be formed adjacent the active tip 70. Three factors in controlling lesion size and shape (lesion geometry) are temperature, time of procedure, and active tip geometry which includes length of the active tip segments and ratios of the segment lengths. In one example the active tip 70 has a length of about 20 mm, and the distal electrode 32, the exposed inner insulator 40, and the proximal electrode 52 have a length ratio L1:L2:L3 of about 7:6:7. A ramp rate of about 10° C./min is used in order to reach a set temperature of about 65° C. to about 70° C. The power is supplied for about 15 minutes, resulting in a lesion having a size of about 30 mm×23 mm, with a lesion volume of about 8.3 cm$^3$.

In another example an active tip 70 with a length of about 30 mm is used, and the distal electrode 32, the exposed insulator 40, and the proximal electrode 52 have a length ratio L1:L2:L3 of about 1:1:1. A ramp rate of about 20° C./min may be used. In one instance of this example, the ramp rate may be used to achieve a set temperature of about 100° C. The power is supplied for about 20 minutes, resulting in a lesion size of about 45 mm×35 mm, with a lesion volume of about 28.9 cm$^3$.

In yet another example, a ramp rate of about 40° C./min is used to achieve a set temperature of about 90° C. Power is applied for about 5 minutes, resulting in a lesion size of about 15 mm×15 mm with a volume of about 1.8 cm$^3$. In some embodiments, the tissue temperature may be maintained at between about 40° C. and about 100° C.

In some cases, the predictability of lesioning is improved by the use of external monitoring electrodes. For example, monitoring an electrode at the periphery of a centrally-formed lesion can help a physician decide when to stop lesioning to ensure an adequate lesion size, or the monitoring electrode could be in communication with a generator with a control program that controls energy delivery. The output of a generator could be controlled by one or more monitoring electrodes such as temperature monitoring electrodes. One example includes placing at least one external temperature sensor at the boundary of a desired lesion, monitoring the at least one external temperature sensor during energy delivery, and determining the lesion is complete when the external temperature reaches a predefined value.

In some embodiments, the power may be delivered at from about 1 Watt to about 100 Watts. In another example power may be delivered at from about 1 Watt to about 50 Watts. In other embodiments, greater than 100 Watts of power may be delivered by the RF energy delivery source. In still another embodiment, less than 1 Watt of power may be delivered. In some embodiments power may be delivered for a duration of between about 2 minutes to about 30 minutes. In other embodiments power may be applied for less than 2 minutes or greater than 30 minutes.

In some embodiments, the ramp rate may range from about 2° C./min to about 100° C./min. In one example, the ramp rate may be about 10° C./min. In another example, ramp rate may be about 20° C./min. In still another example, ramp rate may be about 40° C./min. In one embodiment the ramp rate may be set to optimize the tissue response to achieve the set temperature. This may prevent charring, desiccation or vaporization of tissue. In some embodiments, the power supplied to the bipolar coaxial probe 100 may be less than power supplied to a monopolar probe to achieve an equivalent lesion.

Thus, as described hereinabove, an electrosurgical probe with internal cooling can be particularly useful, for example, in systems and methods for lesioning in bone and other tissue. In some embodiments, the probe is comprised of at least two electrically isolated electrical conductors which are operable to deliver energy in a bipolar manner. One embodiment of such a probe includes an inner conductor inside an outer conductor. The inner electrical conductor includes a lumen for the internal circulation of a cooling fluid. The probe also has an electrical insulator layer between the inner and outer electrical conductors for electrically isolating the electrical conductors. The electrical insulator has sufficient thermal conductivity to allow for cooling of the outside electrical conductor by cooling fluid circulating within the lumen of the inner electrical conductor. Thus, only one conductor is cooled directly, i.e., in contact with the cooling fluid, while the other conductor is indirectly cooled. When used in a system, the probe could enable temperature monitoring to provide data for controlling the delivery of energy through electrodes to tissue and for controlling the flow of cooling fluids to the electrodes.

The embodiments of the invention described above are intended to be exemplary only. The scope of the invention is therefore intended to be limited solely by the scope of the appended claims.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

We claim:

1. An electrosurgical probe for use with a cooling fluid, the electrosurgical probe comprising:
  a distal electrical insulator, a proximal electrical insulator,
    a distal electrical conductor defining a distal electrode with a closed distal end and a proximal electrical conductor defining a proximal electrode, the distal electrode longitudinally spaced apart and electrically isolated from the proximal electrode by the distal electrical insulator;

the distal electrode having a closed proximal end formed by a distal face of the distal electrical insulator to thereby define a closed distal inner lumen for circulating the cooling fluid; and the proximal electrode having a closed distal end formed by a proximal face of the distal electrical insulator and a closed proximal end formed by a distal face of the proximal electrical insulator to thereby define a closed proximal inner lumen for circulating the cooling fluid.

2. The electrosurgical probe of claim 1 further comprising:
a first fluid inlet tube for supplying the closed distal inner lumen and a first fluid outlet tube for exit of the cooling fluid therefrom; and
a second fluid inlet tube for supplying the closed proximal inner lumen and a second fluid outlet tube for exit of the cooling fluid therefrom.

3. The electrosurgical probe of claim 1 wherein a diameter of the distal electrode and the proximal electrode are substantially equal.

4. The electrosurgical probe of claim 1, wherein the distal electrical conductor and the proximal electrical conductor are elongated.

5. The electrosurgical probe of claim 1 further comprising a first temperature sensor.

6. The electrosurgical probe of claim 5 wherein the first temperature sensor is proximate the distal electrode.

7. The electrosurgical probe of claim 5 wherein the first temperature sensor is positioned at the distal electrode.

8. The electrosurgical probe of claim 6, further comprising a protrusion wherein the first temperature sensor is associated with the protrusion isolated from the cooling fluid circulating within the closed distal inner lumen.

9. The electrosurgical probe of claim 5 further comprising a second temperature sensor.

10. The electrosurgical probe of claim 9 wherein the first temperature sensor is proximate the distal electrode and the second temperature sensor is proximate the proximal electrode.

11. The electrosurgical probe of claim 2 wherein, in use, the cooling fluid circulating within the closed distal inner lumen contacts a portion of an inner surface of the distal electrical conductor for direct cooling of the distal electrical conductor.

12. The electrosurgical probe of claim 2 wherein, in use, the cooling fluid circulating within the closed proximal inner lumen contacts a portion of an inner surface of the proximal electrical conductor for direct cooling of the proximal electrical conductor.

13. The electrosurgical probe of claim 1 wherein a thickness of the proximal electrical conductor is substantially constant along its length.

14. The electrosurgical probe of claim 1 wherein a thickness of the distal electrical conductor is substantially constant along its length.

15. The electrosurgical probe of claim 1 wherein a surface area of the distal electrical conductor configured to directly contact the cooling fluid is substantially similar to an area of an outer surface of the distal electrode.

16. The electrosurgical probe of claim 1 wherein a surface area of the proximal electrical conductor configured to directly contact the cooling fluid is substantially similar to an area of an outer surface of the proximal electrode.

17. The electrosurgical probe of claim 1, wherein the electrosurgical probe has an outer diameter of about 13 Gauge to about 17 Gauge.

18. The electrosurgical probe of claim 1, wherein the distal electrode and the proximal electrode are of substantially a same length.

19. The electrosurgical probe of claim 1, wherein the distal electrical conductor and the proximal electrical conductor each have a tubular configuration.

20. The electrosurgical probe of claim 1, wherein each of the distal electrical conductor and the proximal electrical conductor are coupled to an energy supply through electrically conductive insulated wires, wherein the distal face of the proximal electrical insulator defines openings to allow passage of the electrically conductive insulated wires therethrough and the distal face, and the proximal face of the distal electrical insulator each define an opening to allow passage of one of the electrically conductive insulated wires therethrough.

* * * * *